(12) United States Patent
Illsley

(10) Patent No.: US 11,111,403 B2
(45) Date of Patent: Sep. 7, 2021

(54) AQUEOUS ELECTRON BEAM CURABLE COMPOSITIONS COMPRISING POLY(ALKOXYLAES)

(71) Applicant: SUN CHEMICAL CORPORATION, Parsippany, NJ (US)

(72) Inventor: Derek Ronald Illsley, Frome (GB)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 16/971,233

(22) PCT Filed: Jul. 1, 2019

(86) PCT No.: PCT/GB2019/051857
§ 371 (c)(1),
(2) Date: Aug. 19, 2020

(87) PCT Pub. No.: WO2020/012158
PCT Pub. Date: Jan. 16, 2020

(65) Prior Publication Data
US 2021/0087412 A1    Mar. 25, 2021

Related U.S. Application Data

(60) Provisional application No. 62/697,438, filed on Jul. 13, 2018, provisional application No. 62/716,472, filed on Aug. 9, 2018, provisional application No. 62/729,097, filed on Sep. 10, 2018, provisional application No. 62/760,142, filed on Nov. 13, 2018.

(51) Int. Cl.
| | |
|---|---|
| *C09D 11/101* | (2014.01) |
| *B41M 7/00* | (2006.01) |
| *A61L 2/08* | (2006.01) |
| *B41J 11/00* | (2006.01) |
| *B41M 5/50* | (2006.01) |
| *C09D 11/102* | (2014.01) |
| *B41M 5/00* | (2006.01) |
| *C09D 11/033* | (2014.01) |
| *C09D 11/037* | (2014.01) |
| *C09D 11/322* | (2014.01) |
| *C09D 11/38* | (2014.01) |

(52) U.S. Cl.
CPC ............ *C09D 11/101* (2013.01); *A61L 2/087* (2013.01); *B41J 11/002* (2013.01); *B41M 5/0064* (2013.01); *B41M 5/50* (2013.01); *B41M 7/0045* (2013.01); *B41M 7/0081* (2013.01); *C09D 11/033* (2013.01); *C09D 11/037* (2013.01); *C09D 11/102* (2013.01); *C09D 11/322* (2013.01); *C09D 11/38* (2013.01)

(58) Field of Classification Search
CPC ..... C09D 11/101; C09D 11/037; C09D 11/38; C09D 11/322; C09D 11/033; C09D 11/102; B41M 7/0081; B41M 5/0064; B41M 5/50; B41M 7/0045; A61L 2/087; B41J 11/002

See application file for complete search history.

(56) References Cited

U.S. PATENT DOCUMENTS

| | | | |
|---|---|---|---|
| 6,846,851 B2 | 1/2005 | Nakhmanovich | |
| 7,208,257 B2 | 4/2007 | Cheng | |
| 8,292,418 B2 | 10/2012 | Kato | |
| 8,940,811 B2 | 1/2015 | Claes | |
| 9,714,355 B2 | 7/2017 | Illsley | |
| 2009/0301331 A1* | 12/2009 | Laksin | B41M 1/18 101/491 |
| 2013/0041072 A1* | 2/2013 | Sommer | C08G 18/68 523/415 |
| 2018/0022947 A1 | 1/2018 | Lapin | |

FOREIGN PATENT DOCUMENTS

| | | | |
|---|---|---|---|
| EP | 0799871 | 10/1997 | |
| EP | 1734088 | 12/2006 | |
| EP | 2 009 070 A1 | 12/2008 | |
| EP | 2009070 A1 * | 12/2008 | ............ C09D 11/00 |
| EP | 2 636 709 A1 | 9/2013 | |
| EP | 2757118 | 7/2014 | |
| EP | 3 335 896 A1 | 6/2018 | |
| WO | WO 2008/071994 A1 | 6/2008 | |
| WO | WO2016/100085 | 6/2016 | |
| WO | WO2016/207057 | 12/2016 | |
| WO | WO 2017/047615 A1 | 3/2017 | |
| WO | WO2017/144409 | 8/2017 | |
| WO | WO2017/151137 | 9/2017 | |
| WO | WO2017/180491 | 10/2017 | |
| WO | WO2017/180496 | 10/2017 | |
| WO | WO 2018/022590 A1 | 2/2018 | |

OTHER PUBLICATIONS

International Search Report issued in International Application No. PCT/GB2019/051857, dated Sep. 4, 2019.
Written Opinion of the International Searching Authority issued in International Application No. PCT/GB2019/051857, dated Sep. 4, 2019.
International Preliminary Report on Patentability (Chapter II of the Patent Cooperation Treaty) issued in International Application No. PCT/GB2019/051857, dated Jun. 16, 2020.

\* cited by examiner

*Primary Examiner* — Yaovi M Ameh
(74) *Attorney, Agent, or Firm* — Marian E. Fundytus; Ostrolenk Faber LLP.

(57) ABSTRACT

The present application is drawn to aqueous electron beam curable compositions comprising poly(alkylene oxide) containing substances, and any blend of water-soluble or water-dispersible ethylenically unsaturated monomers, oligomers and polymers.

18 Claims, No Drawings

AQUEOUS ELECTRON BEAM CURABLE COMPOSITIONS COMPRISING POLY(ALKOXYLAES)

CROSS REFERENCE TO RELATED APPLICATIONS

The present application is a § 371 National Phase application based on PCT/GB2019/051857 filed Jul. 1, 2019, which claims the benefit of U.S. Provisional Application Nos. 62/697,438, filed Jul. 13, 2018, 62/716,472 filed Aug. 9, 2019, 62/729,097 filed Sep. 10, 2018, 62/760,142 filed Nov. 13, 2018 the subject matter of each of which is incorporated by reference in their entirety.

The present invention describes the most surprising finding that the inclusion of poly(alkylene oxide) containing substances, such as poly(ethylene glycol)s and poly(propylene glycol)s, can promote the EB-curing of aqueous compositions comprising water-dispersible ethylenically unsaturated substances, such as acrylated polyurethane dispersions.

The capacity of such poly(alkylene oxide) containing substances to promote the cure response is not observed when the compositions are cured under the action of UV light, using a suitable photoinitiator. Indeed, as would be anticipated, when such compositions are cured by UV, the resistance properties of the cured compositions are significantly poorer than the comparable compositions which do not contain the substances of the present application, such as poly(ethylene glycol). Substances such as poly(ethylene glycol) are deemed to be inert, as they don't comprise ethylenically unsaturated groups which could take part in the UV-curing reaction. As such, their innately poor solvent resistance contributes to a deterioration of the (solvent) resistance of compositions containing them when cured with UV (using a suitable photoinitiator). Further to this, inclusion of an inert substance will also reduce the crosslink density of a UV-cured composition which will further contribute to poorer solvent resistance of a cured composition.

However, when substances such as poly(ethylene glycol) are included in aqueous compositions further comprising an acrylated polyurethane dispersion, and cured with EB radiation, a very significant improvement in the cure response is observed, as indicated by the improved solvent resistance of the prints. This most surprising finding has significant value, especially for inkjet applications. An issue for the inkjet printing of aqueous compositions comprising polymer dispersions, such as acrylated polyurethane dispersions, is that they usually require the use of a humectant, such as glycerol, to help ensure that the inks do not dry in the printhead causing unwanted blockages. However, humectants such as glycerol have high boiling points and high heats of evaporation and dry very slowly, which limits the printing speed that might be achieved in applications such as the printing of flexible plastic films. The present application addresses this issue by preferably using humectants, such as poly(ethylene glycol), which are not required to be evaporated prior to EB-curing, and themselves contribute to the curing of inventive compositions under the action of EB radiation. Furthermore, substances such as poly(ethylene glycol), poly(propylene glycol) and ethoxylated sorbitan esters, for example, are deemed to be relatively benign, with migration limits into foodstuffs of up to 60 mg per Kg of foodstuff. This, allied with their polymeric nature, makes their use an ideal fit for applications where low migration and safety is highly desirable, such as the printing of food packaging, pharmaceutical packaging, household and personal care packaging, etc.

Although the present application is directed towards inkjet ink compositions in particular, it should be understood that any aqueous EB-curable compositions comprising poly(alkylene oxide) containing substances in combination with water-soluble and/or water-dispersible ethylenically unsaturated materials, such as acrylated polyurethane dispersions, are covered by the present application.

No references describing the benefits of the inclusion of poly(alkoxylates) in aqueous EB-curable compositions, as promoters of the cure response, have been identified. In particular, the use of such water-soluble polymers to promote the cure of aqueous inkjet compositions has not been reported.

U.S. Pat. No. 6,846,851 describes the use of UV-curable humectants as an alternative to typical humectants, such as glycerol and propylene glycol, in compositions which could further comprise polymer dispersions, including acrylated polyurethane dispersions. U.S. Pat. No. 6,846,851 recognised the issue of the slow drying resulting from the use of conventional humectants, such as glycerol and propylene glycol, and proposed polymerizable humectants which did not require evaporation as they would become bound into the UV-cured composition. Thus, the use of materials such as poly(ethylene glycol) diacrylate was disclosed for these UV-curable aqueous compositions. Disadvantages of this UV-curing approach include the need for a photoinitiator to initiate the free radical polymerisation, and the poorer health and safety profile associated with these UV-curable humectants, compared with many of the EB cure promoting poly(alkylene oxide) containing substances of the present application. Poly(ethylene glycol) diacrylates have low migration limits into foodstuffs, presently 10 ppb, and the need for a photoinitiator to enable the UV-curing also poses a migration risk in sensitive printing/coating applications, such as the printing of food packaging. Furthermore, the inventor has separately found that water-soluble acrylated substances, like poly(ethylene glycol) diacrylates, are highly prone to hydrolysis, with the release of acrylic acid, resulting in pH instability of formulated aqueous compositions comprising such materials. U.S. Pat. No. 6,846,851 did not identify, nor allude to, the use of highly involatile humectants such as poly(ethylene glycol) as EB-cure promoting substances. Indeed, by comparing the present application with U.S. Pat. No. 6,846,851, the advantages are clearly apparent.

A real advantage of the present application is that compared with conventional solvent-free UV and EB-curable inkjet compositions which use low molecular weight monomers such as hexanediol diacrylate and dipropylene glycol diacrylate, the risk associated with the migration of ethylenically unsaturated substances is much reduced. This is due to the use of acrylated polymer dispersions, such as acrylated polyurethane dispersions, to provide the crosslinking function. Due to the high molecular weight (preferably greater than 1000 g/mol) of these types of materials they are broadly recognised, as appreciated by those skilled in the art, as having better health and safety profiles, especially with respect to their migration potential, compared with typical monomers used in inkjet printing. This superior safety profile is associated with their significantly higher molecular weights, typically in excess of 2000 (compared with less than 250 for the hexanediol diacrylate and dipropylene glycol diacrylate), which minimises or indeed prevents their migration from UV or EB-cured compositions. The accepted wisdom is that substances whose molecular weights exceed 1000 are not prone to migration, as laid out in EUPIA's "*Guideline on Printing Inks applied to the non-food contact surface of food packaging materials and articles*".

Thus, a particular objective of the present invention is to reduce the amount of contamination from cured inks/coatings in packaging applications. The present invention addresses this problem via the reduction or elimination of migratory compounds which are present in conventional inks/coatings and which cause contamination (i.e. compounds with a low migration limit), and replacing such compounds with compounds which have high migratory limits, while retaining the desired functionality. Surprisingly, the present inventors have found that non-acrylated substances provide a solution to this problem.

A further advantage of the present application over conventional solvent-free UV or EB-curable compositions, such as revealed in U.S. Pat. Nos. 8,940,811 and 9,714,355, is that the lower solid content of the inventive compositions, typically which will be less than 25% (w/w), means that after evaporative drying to remove the water and any other solvent, inkjet compositions prepared according to the present application will deliver significantly lower ink/coating thicknesses, for example 5 microns, or less. This is advantageous for printing/coating applications on thinner plastic films, such as those where the film thickness is 50 microns or less. Furthermore, compared with the compositions revealed in U.S. Pat. Nos. 8,940,811 and 9,714,355 which shrink significantly after UV or EB cure due to the high crosslink density being formed during cure, the inventor has found that compositions of the present application do not shrink anywhere to the same degree, as evidenced by much lower extents of curling and distortion of printed/coated plastic films, such as the 23 micron polyester film used in the examples. This is clearly advantageous for one of the principal intended uses of the present application, namely the printing and coating of food packaging plastic films where any significant distortion of the film during the printing process would be deleterious.

US2018/0022947, discloses the use of water-soluble monomers such as poly(ethylene glycol) diacrylates and more particularly ethoxylated trimethylol triacrylates, in aqueous inkjet compositions, intended for EB-curing. Again, the use of such materials will have the associated disadvantages previously described for U.S. Pat. No. 6,846,851. Although non-reactive polymers such as styrene-acrylic emulsions are disclosed in US2018/0022947, the use of substances according to the present application, such as poly(ethylene glycol)s, and their capacity to enhance the EB-curing response, is neither disclosed nor alluded to. Indeed, the fact that substances, such as poly(ethylene glycol), can promote the EB-cure of aqueous compositions and processes according to the present application, clearly indicates that they take part in the EB-curing process and thereby are reactive in some way. US2018/0022947 describes how EB radiation can be used, in part, to help evaporatively dry aqueous inkjet compositions. It should be understood that the action of EB irradiation may also be used to help dry compositions according to the present application.

WO2017/151137 describes solvent-free EB-curable inkjet compositions comprising hydroxyl-functional monomers, such as hydroxy-butylacrylate, which by way of the description are claimed as being suitable for low migration applications. The use of inert resins such as acrylics is mentioned, but the potential for essentially ethylenically unsaturated free poly(alkylene oxide) containing substances to promote EB-cure is not disclosed.

WO2017/180491 and WO2017/180496 describe solvent-free EB-curable inkjet compositions where the polymerizable component comprises predominantly of multifunctional acrylate monomers. The use of low concentrations of photoinitiators to pin the ink with UV prior to final EB curing was described, as well as the capacity for EB to improve the adhesion to plastic films.

WO2016/100085 describes EB-curable pressure sensitive adhesives which comprise acrylic polymers substituted with acrylate groups to enable free radical polymerisation under EB irradiation.

U.S. Pat. No. 7,208,257, WO2017/144409 and WO2017/157615 all describe how EB curing can be used to enhance the properties of digital toner prints. The improvement in the resistance properties is no doubt due to a degree of polymer crosslinking occurring during the curing process. Indeed, it is well known that EB can be used to crosslink polymers via free radical combination reactions.

As well as US2018/0022947 and U.S. Pat. No. 6,846,851, previously described, EP0799871, U.S. Pat. No. 8,292,418, and EP1734088 also describe UV-curable aqueous inkjet compositions.

EP2757118 describes the preparation of anionic acrylated polyurethane dispersions, which via neutralisation of pendant carboxylic acid groups with metal cations, improves their redispersibility (after drying) making them more suitable for inkjet printing than conventional acrylated polyurethane dispersions. Such acrylated polyurethane dispersions are particularly suited for use in the present application.

WO2018/022590 describes the issues associated with drying radiation-curable inkjet compositions comprising high boiling point humectant solvents such as glycerol and propylene glycol. By the use of water-soluble solvents having lower heats of evaporation, either in combination or not with glycerol or propylene glycol, inks with significantly enhanced drying could be produced. It should be understood that the present application with its use of polymeric humectants, such as poly(ethylene glycol), may also use water-soluble solvent blends in accordance with WO2018/022590.

WO2016/207057 describes an in-line EB-cured digital printing and packaging line where EB is used to sterilise the packaging material during the printing operation to produce aseptic packaging immediately prior to forming and filling the package with foodstuff. However, WO2016/207057 fails to adequately describe a suitable digital printing process to fulfil this disclosure. Therefore, a further aspect of the present application incorporates the in-line printing and sterilisation via EB using compositions according to the present application to produce printed aseptic packaging.

The present application describes a number of examples suitable for inkjet printing, but it should be understood that the present application covers compositions that may be applied by any other coating/printing process where the effect of the inclusion of poly(alkylene oxide) containing substances would be beneficial. Thus, flexographic, printing processes are covered by the present application, as are roller, spray, and other coating methods.

Based upon the identified prior art, the present application would seem to be the first reported instance of the use of water-soluble or dispersible poly(alkylene oxide) containing substances, being essentially free of ethylenically unsaturated groups, to promote the EB-cure of aqueous compositions further comprising monomers, oligomers and/or polymers which are polymerizable by free radical processes.

Thus, according to the present invention there is provided aqueous Electron Beam (EB) curable compositions comprising poly(alkylene oxide) containing substances, which are essentially free of ethylenically unsaturated groups, according to the following expression;

$$R^1[O-(C_nH_{2n}O)_xR^2]_m$$

where $R^1$ and $R^2$ may separately be hydrogen or any organic residue; m can be any number between 1 and 8; n can be any number between 1 and 6, and x can be any number equal to, or greater than 2;
and further comprising any blend of water-dispersible and/or water-soluble ethylenically unsaturated polymers, monomers and/or oligomers.

In a specific embodiment, m=1. All aspects of the following description of the invention are of course applicable to the embodiment where m=1.

It will be appreciated from the disclosure herein that said water-dispersible and/or water-soluble ethylenically unsaturated polymers, monomers and oligomers are free radically polymerizable.

A number of the advantages of the present application over the prior art have already been mentioned.

From the identified prior art, the use of substances containing poly(alkylene oxide) groups, which are essentially free of any ethylenically unsaturated groups, to promote the cure of free-radically polymerizable compositions under the action of electron beam radiation has not been revealed.

A key advantage of the present application over the identified prior art is that involatile humectants such as poly(ethylene glycol)s can be used without the need for their removal prior to the curing process. This is clearly advantageous, as typical humectants such as glycerol, with relatively high boiling points (Glycerol; 290° C.) and heats of evaporation (Glycerol; about 90 kJ/mol), are prone to slow drying, which will limit the press speed that is achievable. The use of poly(ethylene glycol) diacrylates and ethoxylated trimethylolpropane triacrylates as water-soluble polymerizable humectants has been reported, but these compounds suffer from the disadvantages of hydrolysis of the acrylate groups and poorer health and safety profiles compared with poly(ethylene glycol)s, for instance. In respect of any possible contamination of packaged foodstuffs arising from the print or coating, the use of compounds such as poly(ethylene glycol) and poly(propylene glycol) is advantageous since they are generally recognised as being safe. Indeed, poly(ethylene glycol)s are used as components of gelatin capsules intended for human consumption. In the EU, poly(ethylene glycol)s and poly(propylene glycol)s have migration limits of 60 mg/Kg (60 mg per Kg of foodstuff).

It is surprising that the incorporation of highly soluble compounds such as poly(ethylene glycol)s into the EB-curable aqueous compositions of the present application can actually improve the solvent resistance of the cured ink film. This is certainly not observed for analogous compositions cured under the action of UV using a suitable photoinitiator.

Compared with solvent-free EB (or UV) curable compositions, and inkjet compositions especially, the inventive aqueous compositions with their low solid contents, typically 25% (w/w) or less, will enable lower dry film weights after drying and curing. This is advantageous for the printing of flexible packaging films, for example, where plastic films of 50 μm, or less may need to be printed. If an asymmetric print design is produced across the web-width, the high film weights associated with solvent-free EB (or UV) curable inkjet compositions may cause distortion of the reeled web; which is undesirable. Furthermore, the aqueous compositions of the present application cause significantly less distortion/curling of flexible packaging films when compared with solvent-free EB/UV-curable compositions, which is again advantageous. This factor makes compositions according to the present application not only suitable for narrow web printing applications, but also for mid- and wide-web printing applications where the width of the printed film may be 0.5 m, or greater. This makes the present application suitable for the use in a range of flexible film packaging applications, both surface print and reverse print (lamination). Thus, the present application has broad utility in the printing of flexible packaging, as well as suitability for any other printing or coating application involving the EB-cure of aqueous compositions, such as graphics printing.

Yet a further advantage of the present application is with respect to the lack of need for a photointiator to induce the free radical polymerisation. Although photointiators may be used in the inventive compositions, they are not required. Photoinitiators, and their decomposition products, pose a migration risk and presently there is a limited range of photointiators suitable for the use in aqueous inkjet compositions in particular, and more especially photointiators which are suitable for low migration applications. The fact that substances, such as poly(ethylene glycol)s are seen to promote the cure of the inventive aqueous compositions is an indicator that they are involved in the curing reaction. Although not wanting to be bound by any particular hypothesis, the inventor postulates that the improved cure response which is observed is due to the formation of free radicals along the poly(alkylene oxide) chains formed by the action of EB which can initiate the free radical polymerisation of substances comprising ethylenically unsaturated groups. Furthermore, where initiation does not occur from the produced free radicals, any radical-radical recombination termination reactions would also enhance the crosslink density, which again would lead to the improvements in solvent resistance of the cured ink films which have been observed.

The existing commercial digital processes for the printing of flexible packaging films include solvent-free UV-inkjet and electrographic toner (liquid or powder). Many of the advantages described in the technical advantages section also translate to the potential commercial advantages.

Compared with solvent-free UV (or EB) curable inkjet compositions, compositions prepared according to the present application, which other than water and co-solvents, comprising predominantly of polymeric materials, or of substances with high migration limits, are likely to provide a significantly lower migration risk. The lower dry film weights achievable with the present application will be beneficial for the printing of flexible packaging films, more so than is the case with solvent-free UV or EB-curable inkjet compositions.

A limitation associated with the electrographic printing processes is their slow press speeds, typically less than 25 m/min. Since polymeric humectants, such as poly(ethylene glycol)s may be used as the poly(alkylene oxide) containing substance in the present application, there is no need to remove them prior to EB-curing. Thus, the only requirement is for the removal of part of the water, and any other water-soluble solvent, content of the compositions. Thus, it is conceivable that press speeds in excess of 50 m/min will be achievable, especially if the action of the EB irradiation itself, as according to US2018/0022947, can be used to help further dry the inventive compositions.

Another potential advantage of the present application is that EB radiation is also effective at sterilising articles. Therefore, a further potential benefit of the present application is that it will allow for in-line printing and sterilisation of food packaging in a food packaging filling operation. This would be especially useful for aseptic packaging applications. Although Tetrapak have described the outline of such a digital printing process (WO2016/207057) they were not able to disclose any composition or actual printing process that could deliver such a process.

Based on the identified prior art, the use of poly(alkylene oxide) containing substances according to the present application (being essentially free of ethylenically unsaturated groups) to promote the cure of aqueous compositions comprising ethylenically unsaturated material under the action of electron beam irradiation has not been previously described. In particular, the usefulness of the present application with respect to the printing or coating of food packaging articles has not been previously disclosed.

DETAILED DESCRIPTION OF THE INVENTION

The present application is drawn to aqueous electron-beam curable compositions comprising poly(alkylene oxide)-containing substances, and any blend of water-soluble or water-dispersible ethylenically unsaturated monomers, oligomers and polymers. It will be appreciated that the term "any blend of water-soluble or water-dispersible ethylenically unsaturated monomers, oligomers and polymers" means that the composition may comprise one or more of such monomers and/or one or more of such oligomers and/or one or more of such polymers. Particularly favoured ethylenically unsaturated compounds used in the present application include acrylated polyurethane dispersions. The poly(alkylene oxide) components of the said substances may include poly(ethylene glycol)s, poly(propylene glycol)s and higher poly(alkylene oxide)s, and the substances are essentially free of any ethylenically unsaturated groups.

The compositions of the present application are particularly useful for the printing or coating of food packaging and may be applied via any printing or coating method, although inkjet printing is a preferred method. The inventive compositions can be cured with doses of 40 kGy or less and deliver acceptably low levels of unreacted monomer.

Definitions

EB Curing. Compositions prepared according to the present application are suitable for curing under the action of electron beam (EB) radiation. EB curing describes the use of electron beam radiation to polymerize and/or crosslink, any combination of monomers, oligomers and polymers. In the case of the present application the materials used are those which polymerise free radically, and hence contain ethylenically unsaturated groups, such as acrylate.

Low Migration: The compositions of the present application lend themselves to applications including the printing of food packaging, pharmaceutical packaging, personal care and household packaging, display boards in supermarkets, etc. In all these applications it is advantageous that the EB-cured ink, or coating, contains minimal amounts of potentially hazardous uncured material that could leach ('migrate') out of the ink into the surrounding environment thereby causing unwanted contamination. This is of particular concern for food packaging where any contamination of the packaged food from undesirable, migratable, ink components should be minimized.

Molecular Weight: Unless otherwise stated, a reference to "molecular weight" or "average molecular weight" is preferably to the number average molecular weight ($M_n$). The molecular weight can be measured by those techniques known in the art such as gel permeation chromatography. For instance, molecular weight determination may be conducted on a Hewlett-Packard 1050 Series HPLC system equipped with two GPC Ultrastyragel columns, 103 and 104 Å (5 µm mixed, 300 mm×19 mm, Waters Millipore Corporation, Milford, Mass., USA) and THF as mobile phase. Preferably, molecular weight is calculated by comparison with a polystyrene standard.

The term "essentially free of any ethylenically unsaturated groups", as used herein to describe the poly(alkylene oxide) containing substances which are of utility in the present invention, particularly refers to ethylenically unsaturated groups which are, or comprise, acrylate groups. As noted hereinabove, it is surprising that such non-acrylated substances have such utility. It will be appreciated that such non-acrylated poly(alkylene oxide) containing substances may optionally comprise other unsaturated groups, for instance aromatic hydrocarbons, as described elsewhere herein.

The present application describes the most surprising finding that compounds such as poly(ethylene glycol)s and poly(propylene glycol)s can promote the cure of aqueous compositions comprising water-dispersible or water-soluble compounds bearing ethylenically unsaturated groups, such as acrylates, under the action of electron beam (EB) radiation. This surprising finding realizes its effect by delivering ink films, after EB-curing, with significantly enhanced solvent resistance compared with similar compositions free of the inventive compounds. Furthermore, when compositions comprising poly(alkoxylated) compounds according to the present application are cured with UV light, using a suitable photoinitiator, the incorporation of poly(alkoxylated) compounds, such as poly(ethylene glycol) actually causes a reduction in the solvent resistance of the cured film.

It is believed that this previously unrecognized nor anticipated effect of EB cure is due to the poly(alkylene oxide) containing substances of the present application increasing the crosslink density of the ink/coating compositions when cured under the action of EB radiation. This is thought to be due to the poly(alkylene oxide) containing substances producing free radical species when exposed to EB radiation which can initiate the free radical polymerization of ethylenically unsaturated groups. It is possible that substances such as poly(ethylene glycol) can produce a plurality of free radicals along their chemical backbone when exposed to EB radiation, thereby acting as a multifunctional free radical initiator, which would help to increase the crosslink density of the cured ink or coating composition and hence the solvent resistance of the cured print. Furthermore, as well as the potential for free radical initiation from compounds such as PEGs helping to promote the EB cure of the inventive compositions it is also conceivable that radical-radical recombination reactions may also help to promote the cure of the inventive compositions.

This finding, which to the best of the inventor's knowledge has not been previously reported, has particular relevance for applications such as the single pass inkjet printing of food packaging. There are a number of reasons for this. Firstly, materials such as poly(ethylene glycol)s and poly(propylene glycols) are generally regarded as safe, with migration limits (in the EU) of 60 mg/Kg (60 mg of the substance in 1 Kg of foodstuff). Secondly, although photoinitiators may be used in compositions of the present application they are not required, as it is the use of EB which delivers the cure. Photoinitiators and their associated photodecomposition products pose a contamination risk due to the potential for their migrating from any cured ink or coating into the surrounding environment. Thirdly, acrylated polyurethane dispersions ('Ac-PUDs') are a preferred class of ethylenically unsaturated material used in the inventive compositions. Ac-PUDs, being polymeric materials, are not prone to migration, even without any cure. Fourthly, since compounds such as PEGs are used to promote the EB cure of compositions according to the present application, when those compositions are inkjet inks or coatings then the PEG acts as an involatile humectant which helps promote the open time and resolubility of the inkjet composition. Humectants are a key component of aqueous inkjet compositions as they help to prevent the inkjet composition drying in the printhead and causing unwanted blockages. For conventional aqueous inkjet printing onto impervious substrates, such as plastic films, the majority of the humectant and other solvents would need to be removed evaporatively. Failure to do so, would run the risk of poorly dried ink films causing blocking and set-off issues in any reeled, or stacked, printed film. Now, since the use of materials such as PEGs in compositions according to the present application actually take part in the EB-curing process, then they do not need to be removed from the printed ink or coating. The inventor has found that it is possible to incorporate up to 10% (w/w) of a poly(ethylene glycol) into an inkjet composition, which when exposed to EB curing produces a fully dried and tack-free print. This is a significant and unexpected finding which is of significant benefit to the single pass inkjet printing of aqueous inkjet compositions.

The surprising finding of the present application is that the substances comprising poly(alkylene oxide) sub-units which promote the EB-cure of the compositions do so without having any polymerizable (ethylenically unsaturated) groups incorporated into their structure. This most surprising finding has not been disclosed, or alluded to, in the prior art and is one which runs counter to presently perceived wisdom. The inventor does not wish to be bound by any theory as to why this should be the case but conjectures that poly(alkylene oxide) containing substances, such as PEGs, are able to act as initiators of free radical polymerization. They may achieve this under the action of EB radiation by the ready formation of free radicals along the poly(alkylene oxide) chain which can initiate the free radical polymerization of ethylenically unsaturated monomers, oligomers and polymers such as acrylated polyurethane dispersions, as used in the examples of the present application.

Regardless of the reason for the enhanced EB-cure response achievable with the substances of the present application, it should be understood that substances comprising any blend of poly(alkylene oxide) groups according to the following general expression (1) may be used:

$$R^1[O-(C_nH_{2n}O)_xR^2]_m \qquad (1)$$

where $R^1$ may be a hydrogen or any organic residue, and similarly where $R^2$ may be a hydrogen or any organic residue. In this instance an organic residue refers to any possible sub-unit that may be bound to the poly(alkylene oxide) group of the present application and includes, but is not limited to; alkanes, aromatic hydrocarbons, heterocyclics, polyesters, polyamides, polyacrylics, styrene-acrylic copolymers, polyurethanes, polyethers. m can be any number between 1 and 8 (and in a particular embodiment m=1), n can be any number between 1 and 6, and x can be any number equal to, or greater than 2.

The present application is preferably directed to those substances according to expression (2):

$$R^3-(C_nH_{2n}O)_xH \qquad (2)$$

where $R^3$ can be a hydroxyl group or any organic alcohol residue (including other poly(alkylene oxide)s), n can be any number between 1 and 6, and x can be any number equal to, or greater than 2. There is no upper limit on the molecular weight of the substance, but it is preferable that it should be less than 10000, more preferably less than 5000 and most preferably less than 2500.

It should be understood that the present application covers the use of any substance, that is essentially free of acrylate, or other ethylenically unsaturated groups, which comprises as part of its structure a poly(alkylene oxide) sub-unit according to the expressions given above.

Where $R^3$ is a hydroxyl group then non-limiting substances such as poly(ethylene glycol)s, polypropylene glycol)s, poly(butylene glycol)s and poly(tetrahydrofuran)s may be used. Also covered by the present application are substances comprising any blends of these including random and block copolymers comprising poly(ethylene glycol) and poly(propylene glycol), such as the Pluronic range of block copolymer PEG-PPG surfactants supplied by BASF.

Where $R^3$ is an alcohol residue, this may be a mono-alcohol, di-alcohol, tri-alcohol, tetraalcohol, penta-alcohol, hexa-alcohol, or higher alcohol. Non-limiting examples of mono-alcohols, include both aliphatic and aromatic alcohols such as hexanol, octanol, decanol, dodecanol, stearyl alcohol, behenyl alcohol, and any substituted phenol. Non-limiting examples of di-alcohols include aliphatic diols such as neopentyl glycol, propylene glycol, acetylenic diol, ethylene glycol, diethylene glycol, triethylene glycol, 1,2-propanediol, dipropylene glycol, pentane diol, 3-methylpnetane diol, hexane diol, octane diol, etc. It is also conceivable that polyester and polyurethane diols could be used as the diol precursor. Trifunctional alcohols include, but are not limited to trimethylol propane, glycerol. Tetrafunctional alcohols include, but are not limited to pentaerythritol and di-trimethylol propane. Higher alcohols include but are not limited to; dipentaerythritol and sorbitol. It should be understood by those skilled in the art that any suitable alcohol precursor that may be alkoxylated can be used to produce substances according to the present application.

Since the compositions of the present application can be evaporatively dried prior to the EB-curing step it is desirable that the poly(alkoxylate) containing substances of the present application are slow drying. Thus, it is preferred that the boiling point of the poly(alkylene oxide) containing substances have boiling points in excess of 200° C., preferably greater than 220° C., and most preferably greater than 240° C.

As well as the poly(alkylene oxide) containing substances described above, compositions according to the present application also comprise ethylenically unsaturated substances. Acrylated polyurethane dispersions ('Ac-PUDs') are particularly preferred. A non-limiting list of suitable Ac-PUDs includes; Neorad R-440, R-441, R-444, R-447, R-448, R-465, UV-14, UV-20, UV-65, UV-TN6711 (DSM), IRR813, IRR929, IRR929, Ucecoat 2801, Ucecoat 2802 and Ucecoat 2803 (Allnex) Laromer LR8949, LR8983, LR9005, UA 9059, UA9060, UA9064, UA9095, UA9122, EB9100 (BASF) and Bayhydrol UV 2282, UV 2317, UV VP LS 2280, UV VP LS 2317, UV XP 2629, UV XP 2687, UV XP 2689, UV XP 2690, UV XP 2775 (BAYER). The Ac-PUDs used in the present application may be anionically, non-ionically, or cationically stabilized, or a combination of non-ionic and ionically stabilized. Where the Ac-PUDs are anionically stabilized it is preferred that an involatile inorganic base, such as potassium hydroxide, is used to neutralize the Ac-PUD during its manufacture. This approach helps to enhance the resolubility of the Ac-PUD for use in inkjet compositions, as described by WO2014/111349.

There is no restriction on the amount of Ac-PUD (or other ethylenically unsaturated polymer dispersion) that may be used in the inventive compositions. Typically, between 20 and 50% (w/w) of an Ac-PUD would be used, although it would be possible to prepare compositions according to the present application having between about 5 and 90% (w/w) of an Ac-PUD. In the case of compositions intended for inkjet printing it is desirable to minimize the solid content of any ink or coating so as to deliver low dry print film weights. For this reason, it is desirable that the total solid content of any such composition contributed by the polymer component of the Ac-PUD should preferably be the range of 3.0% (w/w) to 25.0% (w/w), that is the dry polymer content provided by the Ac-PUD. As the solid contents of Ac-PUDs are typically in the range of about 30.0 to 40.0% (w/w) this means that the amount of Ac-PUD that might be used in the preparation of an aqueous inkjet composition would be in the range 7.5% (w/w) to 85% (w/w) of the aqueous inkjet ink or coating composition.

It is also possible for a skilled formulator to prepare aqueous compositions according to the present application using other acrylate and non-functional resin technologies. Possibilities in this area would include acrylated polyester dispersions such as the Laromer PE range from BASF; water soluble epoxy acrylates such as Laromer 8765 from BASF and CN132 from Sartomer; styrene maleic anhydride adducts (SMA) where the anhydride group of a styrene-maleic copolymer is reacted with a OH-functional monomer; acetoactate-functional Polymers such as acetoacetate-functional poly(vinyl alcohol) Gohsenx Z from Nippon Gohsei; acrylic emulsions such as those sold under the trade names Joncryl (BASF), Revacryl (Synthomer), Hycar (Lubrizol), Neocryl (DSM), Neboplast (Necarbo), and the Picassian AC range (Picassian Polymers); solution Acrylics such as those sold under the trade names Joncryl (BASF), poly (meth)acrylic acid such as those sold under the trade name Sokalan (BASF); polyurethane dispersions such as those sold under the trade names Neorez (DSM), Sancure (Lubrizol), Syntegra (Dow), Luplen (BASF), and Beetafin (BIP); polyester emulsions such as those sold under the trade names Eastek (Eastman), PVC Emulsions such as those sold under the trade names Vycar (Lubrizol); polyamide dispersions such as those sold under the trade names Casamid (Thomas Swann) and Hydrosize (Michelman); waterbased alkyds such as those sold under the trade names Synaqua (Arkema); poly(vinyl alcohol) such as those sold by Kuraray, Nippon Gohsei & Celanese; polyethylene glycols; poly (vinyl pyrrolidones such as those sold under the trade names PVP-K15, K30, K60, K90 (ISP); maleic Resins such as those sold under the trade names Hydrorez (Lawter); and natural resins such as waterbased shellacs (Worlee), Procote (DOW), and Revertex (Synthomer).

These various resin types may, where applicable, be neutralized using organic bases including but not limited to ammonia, triethylamine, triethanolamine, N-methyldiethanolamine, N,N'-dimethylethanolamine, triisopropanolamine, dimethyl aminoethanol or Arginine. Alternatively, they may be neutralised by an inorganic base including but not limited to alkali metal oxides, alkali metal hydroxides or alkali metal carbonates, with sodium hydroxide or potassium hydroxide being the preferred inorganic bases.

There is no limit on the amount of poly(alkoxylated) containing substances that may be used in compositions prepared according to the present application. However, it is preferable that at least 0.5%, preferably at least 1%, and most preferably at least 2%, by weight of the composition be used. It is preferred that at least 1.0% and no more than 30.0% is used, more preferably from 1.0 to 20.0% and even more preferably from 1.0 to 10.0% by weight of the composition be used.

In a further aspect of the present application, although there is no upper limit of EB dose, compositions of the present application are preferably cured using EB doses of 50 kGy or less, more preferably 40 kGy or less and most preferably with EB doses of 35 kGy or less. Similarly, there is no limit on the accelerating voltage used in generating the EB radiation. However, it is preferable that accelerating voltages of 70 kGy or greater are used. Where compositions of the present application are printed or coated on web fed presses, there is no limit on the minimum press speed. However, especially for inkjet printing, it is preferred that the minimum press speed is 40 m/min or greater, more preferably 50 m/min or greater and most preferably 60 m/min or greater. It should be noted that with developing printhead and EB curing unit technologies that press speeds in excess of 100 m/min could be achievable with compositions prepared according to the present application.

In yet a further aspect to the present application, the inks and coatings may be applied in-line with further packaging converting and (food) filling operations for aseptic packaging.

The ink and coating compositions according to the present application include water. This would preferably not contain ionic impurities and is therefore preferably an ion exchanged or distilled water. The quantity of water used according to the present application, including that which is supplied as part of the raw materials used, is preferably 20 to 90 percent, more preferably 30 to 70 percent by mass according to the entire ink composition.

As well as the poly(alkylene oxide) containing substance of the present application, inks and coatings may also contain one or more water-compatible organic solvents preferably at a level of between 1 and 30 percent, more preferably 1 to 20 percent by mass according to the entire ink composition. Examples of suitable solvents would typically include an alkylene glycol ether or ether acetate type, with the following non-limiting examples; 4-Hydroxy-4-methyl-2-pentanone, diethylene glycol butyl ether, diethylene glycol ethyl ether, diethylene glycol methyl ether, diethylene glycol monoethyl ether acetate, diethylene glycol monopropyl ether, dipropylene glycol ethyl ether, dipropylene glycol methyl ether, ethylene glycol butyl ether, ethylene glycol ethyl ether, ethylene glycol isopropyl ether, ethylene glycol methyl ether, ethylene glycol propyl ether, glycerine carbonate, N-methyl 2-pyrrolidone, propylene glycol, propylene glycol ethyl ether, propylene glycol butyl ether, propylene glycol ethyl ether acetate, propylene glycol methyl ether, propylene glycol n-propyl ether, dipropylene glycol methyl ether, triethylene glycol butyl ether, triethylene glycol methyl ether, tripropylene glycol and tripropylene glycol methyl ether.

Although not required by the present composition, photoinitiators may optionally be included in compositions of the present application to enable dual UV-EB cure, and in that case the total concentration of photoinitiators is preferably less than 5.0% (w/w). Indeed, it is preferred that inventive compositions are essentially free of any photoinitiator. It should be appreciated by those skilled in the art that any combination of photoinitiators, although not necessary, may be included in the inventive compositions. A non-limiting list of possible photoinitiators that could be used includes; α-hydroxyketones such as; 1-hydroxy-cyclohexyl-phenyl-ketone; 2-hydroxy-2-methyl-1-phenyl-1-propanone; 2-hydroxy-2-methyl-4'-tert-butyl-propiophenone; 2-hydroxy-4'-(2-hydroxyethoxy)-2-methyl-propiophenone; 2-hydroxy-4'-(2-hydroxypropoxy)-2-methyl-propiophenone; oligo 2-hydroxy-2-methyl-1-[4-(1-methyl-vinyl)phenyl]propanone; bis [4-(2-hydroxy-2-methylpropionyl)phenyl]methane; 2-Hydroxy-1-[1-[4-(2-hydroxy-2-methylpropanoyl)phenyl]-1,3,3-trimethylindan-5-yl]-2-methylpropan-1-one and 2-Hydroxy-1-[4-[4-(2-hydroxy-2-methylpropanoyl)phenoxy]phenyl]-2-methylpropan-1-one;

acylphosphine oxides such as; 2,4,6-trimethylbenzoyl-diphenylphosphine oxide; ethyl (2,4,6-trimethylbenzoyl) phenyl phosphinate, bis-(2,4,6-trimethylbenzoyl)-phenylphosphine oxide; and bis(2,6-dimethoxybenzoyl)-2,4,4-trimethylpentylphosphinoxide.

α-aminoketones such as; 2-methyl-1-[4-methylthio)phenyl]-2-morpholinopropan-1-one; 2-benzyl-2-dimethyl-amino-1-(4-morpholinophenyl)-butan-1-one; and 2-dimethylamino-2-(4-methyl-benzyl)-1-(4-morpholin-4-yl-phenyl)-butan-1-one; thioxanthones such as; 2-4-diethylthioxanthone, isopropylthioxanthone, 2-chlorothioxanthone, and 1-chloro-4-propoxythioxanthone; benzophenones such as; such as benzophenone, 4-phenylbenzophenone, and 4-methylbenzophenone; methyl-2-benzoylbenzoate; 4-benzoyl-4-methyldiphenyl sulphide; 4-hydroxybenzophenone; 2,4,6-trimethyl benzophenone, 4,4-bis(diethylamino)benzophenone; benzophenone-2-carboxy(tetraethoxy)acrylate; 4-hydroxybenzophenone laurate and 1-[-4-[benzoylphenylsulpho]phenyl]-2-methyl-2-(4-methylphenylsulphonyl)propan-1-one; phenylglyoxylates such as; phenyl glyoxylic acid methyl ester; oxy-phenyl-acetic acid 2-[hydroxyl-ethoxy]-ethyl ester, or oxy-phenyl-acetic acid 2-[2-oxo-2-phenyl-acetoxy-ethoxy]-ethyl ester; oxime esters such as; 1-phenyl-1,2-propanedione-2-(O-ethoxycarbonyl)oxime; [1-(4-phenylsulfanylbenzoyl)heptylideneamino]benzoate, or [1-[9-ethyl-6-(2-methylbenzoyl)carbazol-3-yl]-ethylideneamino] acetate;

Examples of other suitable photoinitiators include diethoxy acetophenone; benzil; benzil dimethyl ketal; titanocen radical initiators such as titanium-bis(η 5-2,4-cyclopentadien-1-yl)-bis-[2,6-difluoro-3-(1H-pyrrol-1-yl) phenyl]; 9-fluorenone; camphorquinone; 2-ethyl anthraquinone; and the like.

An amine synergist may also be optionally included in the formulation. Suitable examples include, but are not limited to, the following:

Aromatic amines such as; 2-(dimethylamino)ethylbenzoate; N-phenyl glycine; benzoic acid, 4-(dimethylamino)-, 1,1'-[(methylimino)di-2,1-ethanediyl]ester; and simple alkyl esters of 4-(N,N-dimethylamino)benzoic acid, with ethyl, amyl, 2-butoxyethyl and 2-ethylhexyl esters being particularly preferred; other positional isomers of N,N-dimethylamino)benzoic acid esters are also suitable;

Aliphatic amines such as N-methyldiethanolamine, triethanolamine and triisopropanolamine;

Also aminoacrylates and amine modified polyether acrylates, including but not limited to; EBECRYL 80, EBECRYL 81, EBECRYL 83, EBECRYL 85, EBECRYL 880, EBECRYL LEO 10551, EBECRYL LEO 10552, EBECRYL LEO 10553, EBECRYL 7100, EBECRYL P115 and EBECRYL P116 available from ALLNEX; CN501, CN550, CN UVA421, CN3705, CN3715, CN3755, CN381 and CN386, all available from Sartomer; GENOMER 5142, GENOMER 5161, GENOMER 5271 and GENOMER 5275 from RAHN; PHOTOMER 4771, PHOTOMER 4967, PHOTOMER 5006, PHOTOMER 4775, PHOTOMER 5662, PHOTOMER 5850, PHOTOMER 5930, and PHOTOMER 4250 all available from IGM, LAROMER LR8996, LAROMER LR8869, LAROMER LR8889, LAROMER LR8997, LAROMER PO 83F, LAROMER PO 84F, LAROMER PO 94F, LAROMER PO 9067, LAROMER PO 9103, LAROMER PO 9106 and LAROMER P077F, all available from BASF; AGISYN 701, AGISYN 702, AGISYN 703, NeoRad P-81 and NeoRad P-85 ex DSM-AGI.

Polymeric photoinitiators and sensitizers may also suitable, including, for example, polymeric aminobenzoates (GENOPOL AB-1 or AB-2 from RAHN, Omnipol ASA from IGM or Speedcure 7040 from Lambson), polymeric benzophenone derivatives (GENOPOL BP-1 or BP-2 from RAHN, Omnipol BP, Omnipol BP2702 or Omnipol 682 from IGM or Speedcure 7005 from Lambson), polymeric thioxanthone derivatives (GENOPOL TX-1 or TX-2 from RAHN, Omnipol TX from IGM or Speedcure 7010 from Lambson), polymeric aminoalkylphenones such as Omnipol 910 from IGM; polymeric benzoyl formate esters such as Omnipol 2712 from IGM; and the polymeric sensitizer Omnipol SZ from IGM.

It should be understood by those skilled in the art that if photoinitiators are included in any composition prepared according to the present application to enable dual UV/EB curing, then they can be incorporated using suitable dispersion approaches, such as those revealed in U.S. Pat. Nos. 4,965,294, 5,168,087 and EP2703458.

Although ethylenically unsaturated polymer dispersions, especially Ac-PUDs, are the preferred free radically polymerizable component of the inventive compositions it should be understood that any blend of free radically polymerizable monomers and oligomers may also be used.

Examples of suitable monofunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts:

isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxy-ethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

Examples of suitable multifunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts:

1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis [oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaacrylate; dipentaerythritol hexaacrylate; ethoxylated dipentaerythritol hexaacrylate.

Examples of monomers comprising free-radically polymerizable groups other than acrylate include N-vinyl amides. Examples of N-vinyl amides include but are not limited to N-vinylcaprolactam (NVC), N-vinyl pyrollidone (NVP), diacetone acrylamide, N-vinyl carbazole, N-acryloxyoxy ethylcyclohexanedicarboximide, N-vinyl imidazole, N-vinyl-N-methylacetamide (VIMA) or acryloyl morpholine (ACMO). Vinyl ethers such as 2-(2-vinyloxyethoxy)ethyl (meth)acrylate (VEEA, VEEM), diethylene glycol divinyl ether (DVE2), triethylene glycol divinyl ether (DVE3), ethyl vinyl ether, n-butyl vinyl ether, iso-butyl vinyl ether, tert-butyl vinyl ether, cyclohexyl vinyl ether (CHVE), 2-ethyl-hexyl vinyl ether (EHVE), dodecyl vinyl ether (DDVE), octadecyl vinyl ether (ODVE), 1-2-butanediol divinyl ether (BDDVE), 1-4,cyclohexanedimethanol divinylether (CHDM-di), hydroxybutyl vinylether (HBVE), 1-4-cyclohexanedimethanolmono vinylether (CHDM-mono), 1,2,4-trivinylcyclohexane (TVCH), vinylphosphonic acid dimethylester (VPA) or vinylphosphonic acid dimethyl ester (VPADME).

As well as, or in place of, free radically-polymerizable monomers any concentration and type of free-radically polymerizable oligomer, including but not restricted to polyurethane acrylates, polyester acrylates, polyether acrylates and epoxy acrylates may be used.

If monomers and/or oligomers are used in the preparation of compositions according to the present application then it is preferable that 25% (w/w) or less, more preferably 15% (w/w) or less and even more preferably 10% (w/w) or less should be used. Those skilled in the art will appreciate that suitable dispersion methods may be used to incorporate any monomer or oligomer into the inventive compositions; such as those revealed in U.S. Pat. Nos. 6,326,419, 6,423,038, 6,011,078 and EP3156462.

Since the products of the present application are primarily waterbased in nature it is also preferable to include a biocide or anti-mold agent. Suitable examples include products based on the following biocide structural types; benz-iso-thiazolinone, Bromo-nitro-propane-diol, isothiazolinone, ethylenedioxydimethanol, or Iodo-propynyl butyl carbamate, which are marketed under the trade names Intercide (Akcros Chemicals) or Nipacide (Clariant). Other types of biocide that could be considered include sodium dehydroacetate (Geogard 111S from Lonza), sodium benzoate (Vancide 51 from R. T. VANDERBILT), sodium pyridinethiol-1-oxide (Sodium Omadine from Arch Chemicals), Sodium salt of o-phenylphenol (Dowicide A from DOW Chemical) and ethyl p-hydroxybenzoate (Nipastat Sodium from Aako). These are preferably used at an amount of 0.01 to 1.00% by mass in the ink composition.

Defoamers can also optionally be included in the formulation; these prevent the formation of foam during manufacture of the ink and also while jetting. These are particularly important with recirculating printheads. Examples of suitable defoamers include TEGO FOAMEX N, FOAMEX 1488, 1495, 3062, 7447, 800, 8030, 805, 8050, 810, 815N, 822, 825, 830, 831, 835, 840, 842, 843, 845, 855, 860, and 883, TEGO FOAMEX K3, TEGO FOAMEX K7/K8 and TEGO TWIN 4000 available from EVONIK. Available from BYK is BYK-066N, 088, 055, 057, 1790, 020, BYK-A 530, 067A, and BYK 354. The additives, DC62, DC65, DC 68, DC71 and DC74 are available from Dow Corning. Agitan 120, 150, 160, 271, 290, 298, 299, 350, 351, 731, 760, 761, 777 are available from Munzing. Surfynol 104PA, AD01, DF-110, DF-58, DF-62, DF-66, DF-695, Df-70, MD-20 are available from Air Products.

Surface control additives are often optionally used to control the surface tension of the ink which is required to adjust the wetting on the face plate of the printhead and also to give the desired drop spread on the substrate or in the case of multi pass inkjet printing, wet on dry drop spread. They can also be used to control the level of slip and scratch resistance of the coating. Examples of suitable surface control additives include but are not limited to TEGO FLOW300, 370, 425, TEGO GLIDE 100, 110, 130, 406, 410, 411, 415, 420, 432, 435, 440, 482, A115, B1484, TEGO GLIDE ZG 400, TEGO RAD2010, 2011, 2100, 2200N, 2250, 2300, 2500, 2600, 2650, 2700, TEGO TWIN 4000, 4100, TEGO WET 240, 250, 260, 265, 270, 280, 500, 505, 510 and TEGO WET KL245 all available from EVONIK. Available from BYK are BYK 333, 337, BYK UV3500, BYK 378, 347, 361, BYK UV3530, 3570, CERAFLOUR 998, 996, NANOBYK 3601, 3610, 3650 and CERMAT 258. From CYTEC EBECRYL 350, 1360, MODAFLOW 9200, EBECRYL 341. From SARTOMER the aliphatic silicone acrylate CN9800 may be used. Surfynol 104, 420, 440, 465, 485, 61, 82, 2502 are available from Air Products. Multiwet BD, EF, SU, SO, VE are available from Croda. Capstone FS-30, 31, 34, 35, 50, 51, 60, 61, 63, 64, 65, 3100 are available from Du Pont.

Included in the ink formulation can optionally be a suitable de-aerator, these prevent the formation of air inclusions and pinholes in the cured coating. These also reduce rectified diffusion, which can cause reliability issues in the printhead. Examples include the following products available from EVONIK: TEGO AIREX900, 910, 916, 920, 931, 936, 940, 944, 945, 950, 962, 980, and 986.

The ink compositions of the present application may optionally contain one or more colorants, including pigments and/or dyes. Examples of suitable organic or inorganic pigments include carbon black, zinc oxide, titanium dioxide, phthalocyanine, anthraquinones, perylenes, carbazoles, monoazo and disazobenzimidazoles, rhodamines, indigoids, quinacridones, diazopyranthrones, dinitranilines, pyrazoles, diazopyranthrones, dinityanilines, pyrazoles, dianisidines, pyranthrones, tetracholoroisoindolines, dioxazines, monoazoacrylides and anthrapyrimidines. The dyes include but are not limited to azo dyes, anthraquinone dyes, xanthene dyes, azine dyes, combinations thereof and the like.

Commercial organic pigments classified according to Color Index International according to the following trade designations, blue pigments PB1, PB15, PB15:1, PB15:2, PB15:3, PB15:4, PB15:6, PB16, PB60; brown pigments PB5, PB23, and PB265; green pigments PG1, PG7, PG10 and PG36; yellow pigments PY3, PY14, PY16, PY17, PY24, PY65, PY73, PY74 PY83, PY95, PY97, PY108, PY109, PY110, PY113, PY128, PY129, PY138, PY139, PY150, PY151, PY154, PY155, PY156, PY175, PY180, PY185 and PY213; orange pigments P05, P015, P016, P031, P034, P036, P043, P048, P051, P060, P061 and P071; red pigments PR4, PR5, PR7, PR9, PR12, PR22, PR23, PR48, PR48:2, PR49, PR112, PR122, PR123, PR149, PR166, PR168, PR170, PR177, PR179, PR190, PR202, PR206, PR207, PR224 and PR254: violet pigments PV19, PV23, PV32, PV37 and PV42; black pigments.

The pigments are milled to typically less than 1 micrometer with a preferred particle size distribution of 10-500 nm, more preferably 10-350 nm to have better transparency and a wide color gamut.

In order to incorporate the above-described pigments to the inventive compositions, it is preferable that the pigments are manufactured and stably stored as a pigment concentrate in water. This is typically achieved by dispersing the pigment using a water-soluble and/or a water-dispersible surfactant which introduces hydrophilic functional groups onto the surface of the pigment particles. Examples of these dispersing resins are numerous and could include polyvinyl alcohols, polyacrylic acid, acrylic acid-acrylonitrile copolymers, vinyl acetate-acrylate copolymers, acrylic acid-acrylate copolymers, styrene-acrylic acid copolymers, styrene-methacrylic acid copolymers, styrene-methacrylic acid-acrylate copolymers, styrene-alpha methyl styrene-acrylic acid copolymers, styrene-alpha methyl styrene-acrylic acid-acrylate copolymers, styrene-maleic acid copolymers, styrene-maleic anhydride copolymers, vinyl naphthalene-acrylic acid copolymers, vinyl naphthalene-maleic acid copolymers, vinyl acetate-maleate copolymers, vinyl acetate-crotonic acid copolymers, and vinyl acetate-acrylic acid copolymers, and the salts thereof. The copolymers can be used in any form of random copolymer, block copolymer, alternating copolymer and graft copolymer. Examples of such resins includes Joncryl 67, 678, 8500, 586, 611, 680, 682, 683 and 69 available from BASF. Examples of the salts include sodium hydroxide, potassium hydroxide and salts of basic compounds such as ammonia, ethylamine, diethanolamine, triethanolamine, propylamine, isopropylamine, dipropylamine, butylamine, isobutyl amine, diethanolamine, triethanolamine, triisopropanolamine, dimethyl ethanolamine, amino methyl propanol, and morpholine. The amount of the basic compound is not strictly limited as long as the resin dispersant is equal to or more than the neutralization equivalent.

Examples of these surfactants used for the pigment dispersion include anionic surfactants such as alkane sulphonates, alpha-olefin sulphonates, alkyl benzene sulphonates, alkyl naphthalene sulphonates, acyl methyl taurinates, dialkyl sulfosuccinates, alkyl sulfates, sulfurized olefins, polyoxyethylene alkyl ether phosphates, polycarboxylic acids and mono glycerol phosphate, amphoteric surfactants such as alkilpyridinium salts and non-ionic surfactants such as polyoxyethylene alkyl ethers, polyoxyethylene alkyl phenyl ethers, polyoxyethylene alkyl esters, polyoxyethylene alkyl amides, glycerol alkyl esters and sorbitan alkyl esters. Examples include EFKA 1000, 4000, 5000 and 6000 series products from BASF, Tamol series products from Dow, and Solsperse 27,000, 40,000, 44,000, 46,000 and 47,000 from Lubrizol.

The EB-curable compositions of the present application may also contain other components which enable them to perform in their intended application. These other ink components include, but are not restricted to; stabilizers, wetting aids, slip agents, inert resins, antifoams, fillers, rheological aids, amine synergists, etc.

Where inventive compositions are applied to the (non-contact) surface of primary or secondary packaging intended for foodstuffs, then any contamination from the package impacting the foodstuff should fall within the guidelines set out by Article 3 of Regulation (EC) No 1935/2004 (supplemented by EC No 10/2011), as recommended by EUPIA, requiring that materials and articles in contact with food;

"shall be manufactured in accordance with good manufacturing practices, so that under normal or foreseeable conditions of use, they do not transfer their constituents to food in quantities which could.
    endanger human health; or
    bring about an unacceptable change in the composition of the food; or
    bring about a deterioration in the organoleptic characteristics thereof"

EUPIA has recommended that Article 3 of this provision be followed when producing printed matter for food packaging and has produced a detailed guideline for the selection of raw materials intended for printing inks for food packaging, along with guidelines on the testing of printed matter to ensure that regulatory requirements are achieved. Where no SML exists for a specific component then the following migration limits apply;

"A target migration limit of no concern for non-evaluated substances of 10 ppb is the ultimate objective, to be consistent with other food contact materials.

In particular, a substance is acceptable if its specific migration does not exceed:
    10 ppb, in case of insufficient toxicological data
        50 ppb if three negative mutagenicity tests requested by EFSA4 Guidelines are available above 50 ppb, if supported by favorable toxicological data and/or evaluation done in accordance with the EFSA Guidelines" (Extract from EuPIA Guideline on Printing Inks applied to the non-food contact surface of food packaging materials and articles, September 2009)

EUPIA also provides guidelines on how to measure the potential level of migratables arising from printed matter. For inks and coatings applied to the non-food contact surface of packaging (i.e. the outer surface), whether that be to the primary packaging or secondary packaging (labels and sleeves) then the most likely route for migratable species from the ink contaminating the foodstuff is by what is known as set-off migration. This is where printed matter is stacked or reeled prior to it being filled with food. Thus, the ink comes into contact with what will be the food-contact surface of the package and migratable components of the ink can diffuse into this surface. When the package is then filled with foodstuff, the contaminants from the ink which have diffused into the contact-surface of the package can then leach into the food causing a potential contamination issue.

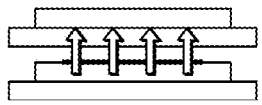

Thus, any energy-curable fluid which is applied to either the primary or secondary packaging of foodstuff should not result in contamination of that foodstuff at levels exceeding the limits detailed above.

The present application further encompasses the following relationship between the electron beam dose, the accelerating voltage used and the press speed.

$$X=(A \cdot B/C)<100$$

Where A is the EB dose in kGy, B is the accelerating voltage in keV and C is the press speed in m/min.

Furthermore, an aspect covered by the present application is the use of the electron beam radiation to facilitate other beneficial processes in the production of food packaging, in particular. Thus, the application of electron-beam curable primers, varnishes and adhesives in-line with inks and coatings of the present application are also covered by the present application in terms of their being applied prior to and after the printing of the inks and coatings described by the present application. In particular, the use of electron beam to improve the resistance of gas barrier coatings comprising poly(vinyl alcohol) or ethylene-vinyl alcohol copolymers applied as either a primer layer or as an overprint varnish are covered by the present application. This has the benefit of improving the resistance of such gas barrier coatings to water and steam and also improves their oxygen barrier performance, in particular, at high relative humidities, especially those in excess of 50%. The use of electron-beam curable adhesives in the preparation of multilayer plastic laminates is also covered by the present application. This is an important factor for the flexible packaging market where lamination of several plies of flexible plastic film are required to deliver the required properties of the food packaging. The use of an electron-beam curable adhesive will allow the rapid generation of stable plastic laminate films; enabling the rapid delivery of finished printed plastic laminate films into the supply chain. This is clearly advantageous for digital printing where rapid turnaround is required, and would be an issue with the use of conventional adhesives, such as the 2-pack isocyanates, which can take a number of days to fully cure. The use of conventional adhesives, requiring laminates to be stored for a number of days before delivery, would limit the utility of digital printing in this sector as it would remove a key advantage of digital printing, namely the fast turnaround and short delivery times.

According to a further aspect of the invention, there is provided the use of poly(alkylene oxide) containing substances as defined in claim 1 to promote the EB-cure of free-radically polymerizable compositions which contain water-dispersible and/or water-soluble ethylenically unsaturated components, particularly selected from any blend of water-dispersible and/or water-soluble ethylenically unsaturated polymers, monomers and oligomers, i.e. any blend of water-dispersible and/or water-soluble ethylenically unsaturated polymers, monomers and/or oligomers. The foregoing description of the other aspects of the invention, including the preferences thereof, is equally applicable to this aspect of the invention too.

According to a further aspect of the present invention there is provided a process for preparing a printed substrate comprising printing the composition as defined hereinabove onto a substrate and curing, preferably using electron beam, preferably using an EB dose ≤50 kGy and an accelerating voltage ≥70 kev. It will be appreciated that the foregoing description of the other aspects of the invention, including the preferences thereof, is equally applicable to this aspect of the invention too.

According to a further aspect of the present invention there is provided a printed article comprising a composition as defined hereinabove and/or which is obtainable by the printing process as defined hereinabove. Thus, it will be appreciated that the printed article in particular comprises a cured coating derived from a curable composition as defined hereinabove. The article preferably comprises a substrate which is a plastic film. The printed article is preferably a food packaging article. It will be appreciated that the foregoing description of the other aspects of the invention, including the preferences thereof, is equally applicable to this aspect of the invention too.

The present application is further described by the examples given below.

The present invention has been described in detail, including the preferred embodiments thereof. However, it will be appreciated that those skilled in the art, upon consideration of the present disclosure, may make modifications and/or improvements on this present application that fall within the scope and spirit of the present application.

Examples

The following examples illustrate specific aspects of the present application and are not intended to limit the scope thereof in any respect and should not be so construed.

Ink and Print Preparation

The inks were prepared by blending the components with a Silverson disperser for 5 minutes.

The inks were then applied to 23 μm Melinex 813 (polyester film, ex. Hi-Fi Films) at 8 μm using a calibrated K-Bar (ex. RK Print). The inks were then dried under a warm flow of air (using a portable hair dryer) for 10 seconds before they were cured.

A Comet ebeam EBLab was used to cure the inks; this unit has a maximum beam energy of 200 keV with doses up to 450 kGy in a single pass possible. Nitrogen inertion was applied until the oxygen level was <200 ppm, and the prints were cured with a dose of 30 kGy, using an accelerating voltage of 100 keV.

Assessing the Degree of Cure

The effectiveness of the cure was determined by assessing the solvent resistance of the prints. This involved rubbing the print surface with a cotton bud soaked in isopropyl alcohol and determining the number of rubs required to cause visible disruption of the print. The results were recorded as the number of double rubs required to disrupt the individual prints.

Ink Composition

All the inks were prepared according to the following composition.

TABLE 1

Basic ink formulations. Specific formulations are identified in the ensuing table.

| Component | Weight % |
|---|---|
| Deionized Water | 41.0-47.6 |
| Dowanol DPM | 8.0 |
| Dowanol PnB | 2.0 |
| Amietol M12 | 0.2 |
| TegoWet KL245 | 0.2 |
| Ac-PUD | 30.0 |
| Polyalkoxylate | 0-6.0 |
| Cyan Pigment Dispersion | 12.0 |
| (Irgacure 2959) | 0-0.6 |

Notes to Table 1:
Dowanol DPM = dipropylene glycol methyl ether, ex. Dow
Dowanol PnB = propylene glycol n-butyl ether, ex. Dow
Amietol M12 = N-methyldiethanolamine, ex. Eastman
Tegowet KL245 = polyether siloxane copolymer, ex. Tego
Ac-PUD = Two acrylated polyurethane dispersions were used in this study, Neorad R448 (ex. DSM) and IRR929, ex. Allnex.
Polyalkoxylate = a range of polyalkoxylate compounds were investigated, and these are described in Table 2.
Cyan Pigment Dispersion = a proprietary aqueous dispersion comprising 21% (w/w) of cyan pigment 15:4.
Irgacure 2959 = water-soluble photoinitiator, ex. IGM Resins. This photoinitiator was used in the control formulations cured under the action of UV. The inks were cured by UV, cured at 200 mJ/cm$^2$, using a Fusion UV Systems UV-Rig equipped with a medium pressure H-bulb. The belt speed was adjusted to deliver the required UV-dose of 200 mJ/cm$^2$, as measured by a calibrated International Light Technologies ILT 490 Profiling Belt Radiometer (covering the UV-A and UV-B ranges).

Table 2 shows the results for inks prepared using Brij L9 (Polyoxyethylene (9) lauryl ether), a non-ionic surfactant supplied by Croda.

It is clear from the results given in Table 2 that the Inventive compositions comprising the poly(alkoxylate) substance, Brij L9, demonstrate significantly superior cure performance when cured by EB than those compositions without the poly(alkoxylate) also cured with EB. Furthermore, as expected, the inclusion of such a polyalkoxylate containing substance into a UV-curable aqueous composition significantly degrades the observed solvent resistance of the cured print.

Table 3 provides the results for a series of inks based on the Ac-PUD Neorad R448, and a variety of poly(alkoxylate) containing substances at different concentrations.

TABLE 3

Impact of Different Poly(alkoxylate) Containing Substances on the EB-Cure of Aqueous Inks Comprising An Ac-PUD

| | Poly (Alkoxylate) | % (w/w) of Polyalkoxylate | IPA Solvent Resistance (EB Cured Ink) |
|---|---|---|---|
| Comparative Example 1 | — | — | 25 |
| Inventive Example 3 | Brij L9 | 0.25 | 35 |
| Inventive Example 4 | Brij L9 | 0.5 | 50 |
| Inventive Example 1 | Brij L9 | 1.0 | 65 |
| Inventive Example 5 | Brij L9 | 2.0 | 35 |
| Inventive Example 6 | Brij L9 | 4.0 | 30 |
| Inventive Example 7 | Brij L4 | 1.0 | 30 |
| Inventive Example 8 | Brij Oleth-10 | 1.0 | 40 |
| Inventive Example 9 | Brij Oleth-20 | 1.0 | 35 |
| Inventive Example 10 | Triethylene Glycol | 0.5 | 50 |
| Inventive Example 11 | Triethylene Glycol | 1.0 | >100 |
| Inventive Example 12 | Triethylene Glycol | 2.0 | >100 |
| Inventive Example 13 | Triethylene Glycol | 4.0 | 60 |
| Inventive Example 14 | Triethylene Glycol | 6.0 | 50 |
| Inventive Example 15 | PEG200 | 0.5 | 50 |
| Inventive Example 16 | PEG200 | 1.0 | >100 |
| Inventive Example 17 | PEG600 | 0.5 | 50 |
| Inventive Example 18 | PEG1000 | 0.5 | 50 |
| Inventive Example 19 | PEG1450 | 0.5 | 50 |

TABLE 2

Aqueous Ink Compositions Showing the Benefit of Including a poly (alkoxylate) containing substance in compositions cured by EB

| | Ac-PUD | Poly (Alkoxylate) | % (w/w) Poly (Alkoxylate) | Irgacure 2959 | IPA Solvent Resistance (EB Cured Ink) | IPA Solvent Resistance (UV Cured Ink) |
|---|---|---|---|---|---|---|
| Comparative Example 1 | R448 | — | — | — | 25 | — |
| Comparative Example 2 | R448 | — | — | Y | — | 50 |
| Inventive Example 1 | R448 | Brij L9 | 1.0 | — | 65 | — |
| Comparative Example 3 | R448 | Brij L9 | 1.0 | Y | — | 15 |
| Comparative Example 4 | IRR929 | — | — | — | 50 | — |
| Comparative Example 5 | IRR929 | — | — | Y | — | 60 |
| Inventive Example 2 | IRR929 | Brij L9 | 1.0 | — | >100 | — |
| Comparative Example 6 | IRR929 | Brij L9 | 1.0 | Y | — | 50 |

TABLE 3-continued

Impact of Different Poly(alkoxylate) Containing Substances on the EB-Cure of Aqueous Inks Comprising An Ac-PUD

| | Poly (Alkoxylate) | % (w/w) of Polyalkoxylate | IPA Solvent Resistance (EB Cured Ink) |
|---|---|---|---|
| Inventive Example 20 | PPG400 | 0.5 | 30 |
| Inventive Example 21 | PPG1000 | 0.5 | 60 |

The results in Table 3 again clearly demonstrate how the inclusion of poly(alkoxylate) containing substances into inventive compositions further comprising an acrylated polyurethane dispersion can significantly improve the cured ink properties, as indicated by the increased solvent resistance of the cured prints compared with Comparative example 1, comprising no poly(alkylene oxide) containing substance. Inventive example 14 shows that relatively high concentrations of triethylene glycol ('TEG'), an involatile humectant solvent (boiling point=285° C.) commonly used in the preparation of aqueous inkjet compositions, can be incorporated into inventive compositions. This is an important finding for the preparation of single pass aqueous inkjet fluids, where the slow drying of such humectants would likely restrict the press speed achievable for compositions not cured by EB. A further observation made with all the inventive examples was that they cured to provide tack-free surfaces.

To further show the advantages attendant to compositions and processes of the present application Inventive examples 10 to 14 were re-made as UV-curable compositions, by the inclusion of 0.6% (w/w) Irgacure 2959 as previously described. The inks were applied, dried and cured as described previously. Table 4 provides the results for the solvent resistance and physical nature of the prints cured by both EB and UV.

TABLE 4

Comparison of Inks Comprising TEG and Cured by either EB or UV.

| | % (w/w) TEG | Irgacure 2959 | EB or UV-Cured | Solvent Resistance | Print Physical Appearance |
|---|---|---|---|---|---|
| Comparative Example 1 | 0 | — | EB | 25 | Tack-free |
| Comparative Example 2 | 0 | Y | UV | 50 | Tack-free |
| Inventive Example 10 | 0.5 | — | EB | 50 | Tack-free |
| Comparative Example 7 | 0.5 | Y | UV | 45 | Tack-free |
| Inventive Example 11 | 1.0 | — | EB | >100 | Tack-free |
| Comparative Example 8 | 1.0 | Y | UV | 30 | Tack-free |
| Inventive Example 12 | 2.0 | — | EB | >100 | Tack-free |
| Comparative Example 9 | 2.0 | Y | UV | 15 | Slightly tacky print surface |
| Inventive Example 13 | 4.0 | — | EB | 60 | Tack-free |
| Comparative Example 10 | 4.0 | Y | UV | 5 | Tacky Print Surface |
| Inventive Example 14 | 6.0 | — | EB | 55 | Tack-free |
| Comparative Example 11 | 6.0 | Y | UV | 2 | Tacky Print Surface |

Again, the results in Table 4 for the UV-cured comparative examples are what would be expected, according to the accepted state-of-the-art for such compositions when energy-cured. The results obtained for the analogous inventive compositions when cured with EB are unexpected and would likely not be anticipated by those skilled in the art.

What is claimed is:

1. An aqueous Electron Beam (EB) curable composition comprising at least 0.5% (w/w) and no more than 10.0% (w/w) of poly(alkylene oxide) containing substances, which are essentially free of ethylenically unsaturated groups, according to the following expression:

$$R^3-(C_nH_{2n}O)_xH$$

where $R^3$ can be a hydroxyl group or any organic alcohol residue (including other poly(alkylene oxide)s), n can be any number between 1 and 6, and x can be any number equal to, or greater than 2; and further comprising any blend of acrylated polyurethane dispersions.

2. The composition according to claim 1 wherein the molecular weight of the substance is less than 10000, more preferably less than 5000 and most preferably less than 2500.

3. The composition according to claim 1 wherein the poly(alkylene oxide) containing substance can be selected from the group consisting of poly(ethylene glycol), poly(propylene glycol), block copolymers of poly(ethylene glycol) and poly(propylene glycol), alkyl ethers of poly(ethylene glycol), alkyl ethers of poly(propylene glycol), ethoxylated neopentyl glycol, ethoxylated trimethylolpropane, propoxylated trimethylolpropane, ethoxylated pentaerythritol, propoxylated pentaerythritol, ethoxylated di-trimethylolpropane, propoxylated di-trimethylolpropane, ethoxylated di-pentaerythritol, propoxylated di-pentaerythritol, ethoxylated sorbitan esters, ethoxylated acetylenic diols, and combinations thereof.

4. The composition according to claim 1 comprising at least 1.0% (w/w) of the poly(alkylene oxide) containing substance.

5. The composition according to claim 1 in which the acrylated polyurethane dispersion is anionically stabilized.

6. The composition according to claim 1 in which the acrylated polyurethane dispersion is neutralized with an inorganic base.

7. The composition according to claim 1 which is a pigmented inkjet ink.

8. The composition according to claim 1 where the majority of the water is removed evaporatively prior to the electron beam curing step.

9. The composition according to claim 1 which is cured by electron beam radiation with a dose of 50 kGy, or less.

10. The composition according to claim 1 where the EB radiation is produced with an accelerating voltage of 70 keV, or greater.

11. The composition according to claim 1 which has a solids content of less than 25% (w/w).

12. The composition according to claim 1 wherein the composition is essentially free of photoinitiators.

13. The composition according to claim 1 wherein the boiling point of the poly(alkylene oxide) containing substance is in excess of 200° C., preferably greater than 220° C., and most preferably greater than 240° C.

14. A method of printing comprising applying a composition according to claim 1 onto a substrate and curing.

15. The method of claim 14, wherein the substrate is a plastic film.

16. A printing and sterilization method for producing aseptic food packaging, comprising applying the composition of claim 1 onto a substrate and curing.

17. A printed article prepared by the method of claim 14.

18. A printed article according to claim 17 wherein the thickness of the cured composition is 5 microns or less, optionally wherein the substrate thickness is 50 microns or less.

\* \* \* \* \*